US012714913B2

(12) United States Patent
Zoffoli et al.

(10) Patent No.: US 12,714,913 B2
(45) Date of Patent: Aug. 25, 2026

(54) MEASUREMENT STATION AND SYSTEM FOR ASSESSING THE FUNCTIONAL AGE OF A USER

(71) Applicant: TECHNOGYM S.p.A., Cesena (IT)

(72) Inventors: Luca Zoffoli, Cesena (IT); Riccardo Crisci, Cesena (IT); Silvano Zanuso, Cesena (IT); Filippo Montanari, Cesena (IT)

(73) Assignee: TECHNOGYM S.p.A., Cesena (IT)

( * ) Notice: Subject to any disclaimer, the term of this patent is extended or adjusted under 35 U.S.C. 154(b) by 0 days.

(21) Appl. No.: 18/627,668

(22) Filed: Apr. 5, 2024

(65) Prior Publication Data

US 2024/0342553 A1 Oct. 17, 2024

(30) Foreign Application Priority Data

Apr. 12, 2023 (IT) ........................ 102023000007035

(51) Int. Cl.
*A63B 24/00* (2006.01)
*A63B 71/06* (2006.01)
(Continued)

(52) U.S. Cl.
CPC ...... *A63B 24/0062* (2013.01); *A63B 24/0075* (2013.01); *A63B 71/0622* (2013.01);
(Continued)

(58) Field of Classification Search
CPC ............ A63B 24/0062; A63B 24/0075; A63B 71/0622; G16H 40/67; G16H 50/30; G06V 40/10; G06V 40/20
See application file for complete search history.

(56) References Cited

U.S. PATENT DOCUMENTS 9,808,184 B2 11/2017 Sakai et al.
2005/0228239 A1 10/2005 Shallenberger
(Continued)

FOREIGN PATENT DOCUMENTS

CA 2 531 420 1/2005

OTHER PUBLICATIONS

Italian Search Report for IT 10202300007035 dated Oct. 16, 2023.

*Primary Examiner* — Kesha Frisby
(74) *Attorney, Agent, or Firm* — B. Aaron Schulman, Esq.; Stites & Harbison, PLLC

(57) ABSTRACT

Measurement station for assessing the functional age of a user, comprising:
- a display and/or a loudspeaker;
- a controller presenting, via the display and/or the loudspeaker, instructions guiding a user in performing first and second tests for assessing the mobility of the body and the balance ability of the user;
- a camera which sends to the controller images of the user captured during the tests.

The controller performs at least one of:
- calculating first and second functional age values based on the images captured, and an overall functional age value of the user based on the first and second functional age values; or sending the first and second functional age values to a remote controller that calculates an overall functional age value of the user at least based on the functional age values sent;
- sending data related to the images captured to a remote controller that calculates first and second functional age values based on the data received, and an overall functional age value based on the first and second calculated functional age values.

17 Claims, 9 Drawing Sheets

(51) Int. Cl.

*G06V 40/10* (2022.01)
*G06V 40/20* (2022.01)
*G16H 40/67* (2018.01)
*G16H 50/30* (2018.01)

(52) U.S. Cl.

CPC .............. *G06V 40/10* (2022.01); *G06V 40/20* (2022.01); *G16H 40/67* (2018.01); *G16H 50/30* (2018.01); *A63B 2071/0625* (2013.01); *A63B 2220/05* (2013.01); *A63B 2220/807* (2013.01)

(56) References Cited

U.S. PATENT DOCUMENTS

2014/0272853 A1 9/2014 Sakai et al.
2019/0295437 A1 9/2019 Rubinstein et al.
2020/0121259 A1 4/2020 Shin et al.

MEASUREMENT STATION AND SYSTEM FOR ASSESSING THE FUNCTIONAL AGE OF A USER

The present disclosure generally relates to the field of wellness.

In particular, the present disclosure relates to a measurement station and an assessment system for assessing the functional age of a user.

As is known, over the last few decades the so-called world of fitness and subsequently the conceptually broader world of wellness have been subject to a notable expansion.

In fact, an increasingly larger segment of the population began to firstly dedicate more time to physical exercise by frequenting gyms or fitness centres of various types in a more or less assiduous manner, even at an advanced age.

Alongside the purely physical aspect, growing attention has also been drawn towards the psychological aspect, or to that which could be defined as "brain fitness", and the mental and emotional health are nowadays considered by users to be as important as physical health.

Consequently, operators in the sector have thus gradually defined a number of reference parameters and developed various methodologies, equipment and machines suitable for measuring these parameters that are indicative of the physical and/or mental health status of users.

For example, a typical parameter used to assess the physical health status is the so-called Body Mass Index, which is referred to internationally by the acronym 'BMI'. However, this parameter does not provide a correct estimate of body composition with regard to subjects who have high muscle mass. For this purpose, use is made of an alternative technique, that is to say, bioimpedance, which makes it possible to determine in an indirect manner the actual fat and muscle masses of a user.

Another parameter is the so-called $VO_2$max which in essence measures a user's capacity to consume oxygen during physical exertion and is often correlated to or measured together with maximum heart rate.

Currently, there are various types of instruments and devices that measure one or the other of the parameters most commonly used in the field.

In some cases, based on the parameter measured-usually a parameter related to the state of physical fitness, some devices, such as the most recent models of smartwatches, also provide a value indicative of age, which in some cases is referred to as biological age or functional age, or in other words, that which would be, based on the parameter or domain measured, the age of the user in relation to his or her true chronological age which reflects the expected performance capacity for a user for a given age and sex.

However, the solutions currently known, while calculating the functional age of a user, are susceptible of further improvements.

In particular, the value calculated for the assumed functional age, which usually represents a merely indicative value and an end in itself, is computed on the basis of a rather limited and partial data set, and may therefore prove not to be particularly accurate and reliable.

Therefore, according to some aspects, the present disclosure provides a measurement station for assessing the functional age of a user, comprising:

at least one of a display and a loudspeaker;

at least one controller configured to present, via said display and/or said loudspeaker, a plurality of instructions designed to guide a user in performing at least:

a first test adapted to assess a current level of mobility of at least one part of the body of the user;

a second test designed to assess a current level of the balance ability of the user;

a camera configured to capture and send to the controller one or more images of the user when it is performing said first and second tests; and wherein said controller is further configured to perform at least one of the following steps:

(a): calculate a first functional age value based on the one or more images captured while performing the first test, a second functional age value based on the one or more images captured while performing the second test, and thereafter calculate an overall functional age value of the user at least based on said first and second functional age values or send said first and second calculated functional age values to a remote controller configured to calculate an overall functional age value of the user at least based on said first and second functional age values sent;

(b): send data related to said one or more images captured during the execution of the first test and the second test to a remote controller configured to calculate a first and a second functional age values based on the data related to the one or more images captured during the execution of the first and second tests, respectively, and an overall functional age value of the user at least based on said first and second calculated functional age values.

In some further aspects, the present disclosure provides also a system for assessing the functional age of a user, comprising at least:

a measurement station comprising:

at least one of a display and a loudspeaker;

at least one controller configured to present, via said display and/or said loudspeaker, a plurality of instructions designed to guide a user in performing at least:

a first test adapted to assess a current level of mobility of at least one part of the body of the user;

a second test designed to assess a current level of the balance ability of the user;

a camera configured to capture and send to the controller one or more images of the user when it is performing said first and second tests; and wherein said controller is further configured to perform at least one of the following steps:

(a): calculate a first functional age value based on the one or more images captured while performing the first test, a second functional age value based on the one or more images captured while performing the second test, and thereafter calculate an overall functional age value of the user at least based on said first and second functional age values or send said first and second calculated functional age values to a remote controller configured to calculate an overall functional age value of the user at least based on said first and second functional age values sent;

(b): send data related to said one or more images captured during the execution of the first test and the second test to a remote controller configured to calculate a first and a second functional age values based on the data related to the one or more images captured during the execution of the first and second tests, respectively, and an overall functional age value of the user at least based on said first and second calculated functional age values.

a remote controller suitable for being placed in communication with said measurement station;

and wherein said remote controller is configured at least to:

receive in input from the measurement station data related to one or more images captured while performing a first test suitable for assessing a current level of mobility of at least one part of the body of the user, and a second test suitable for assessing a current level of the balance ability of the user;

calculate a first and a second functional age values on the basis of said data related to the one or more images captured during the performance of the first and second tests, respectively, and an overall functional age value of the user at least on the basis of said calculated first and second functional age values.

The particular embodiments form the subject matter of the dependent claims, the contents of which are to be understood as constituting an integral part of the present description.

Additional characteristic features and advantages of the disclosure will become apparent from the detailed description that follows, which is provided purely by way of non-limiting example, with reference to the appended drawings, in which.

Figure 1:
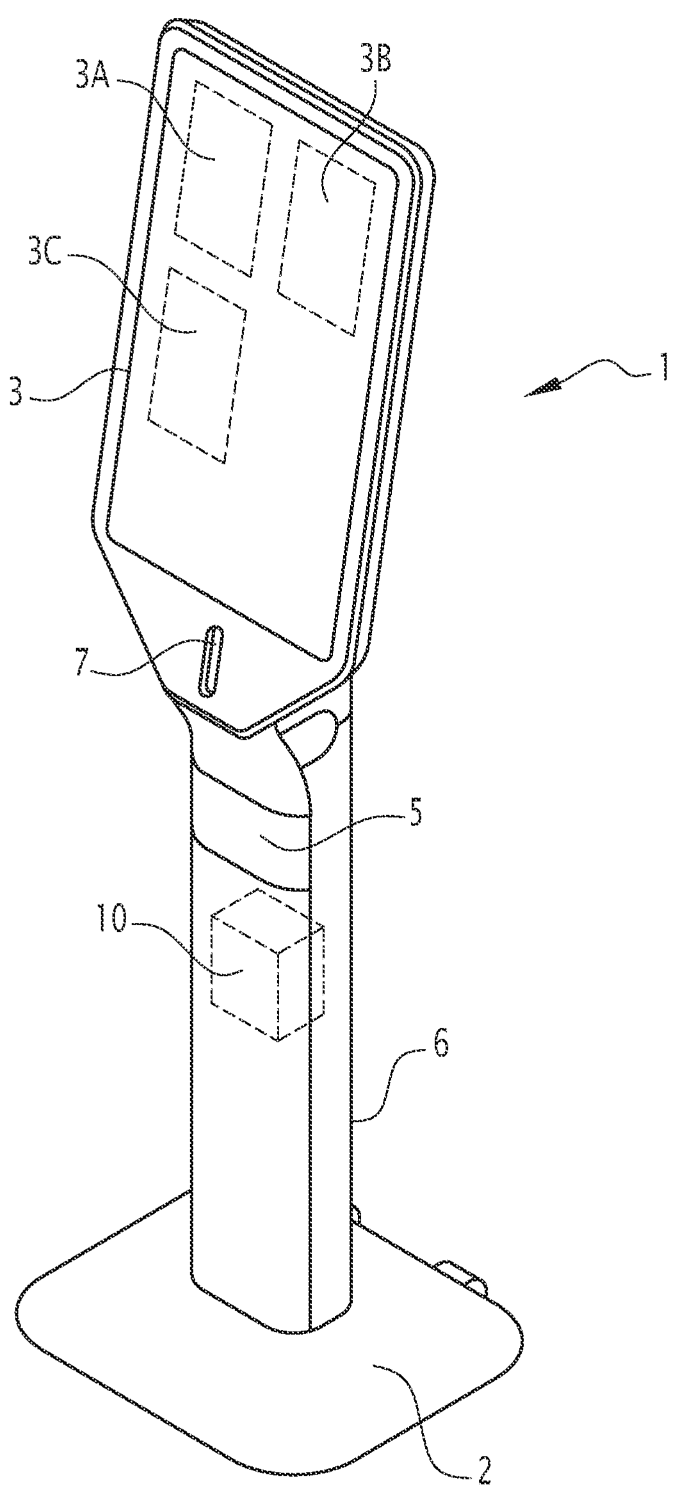
FIG. 1 is a perspective view illustrating one possible embodiment of a measurement station for assessing the functional age of a user according to the present disclosure.
Figure 2:
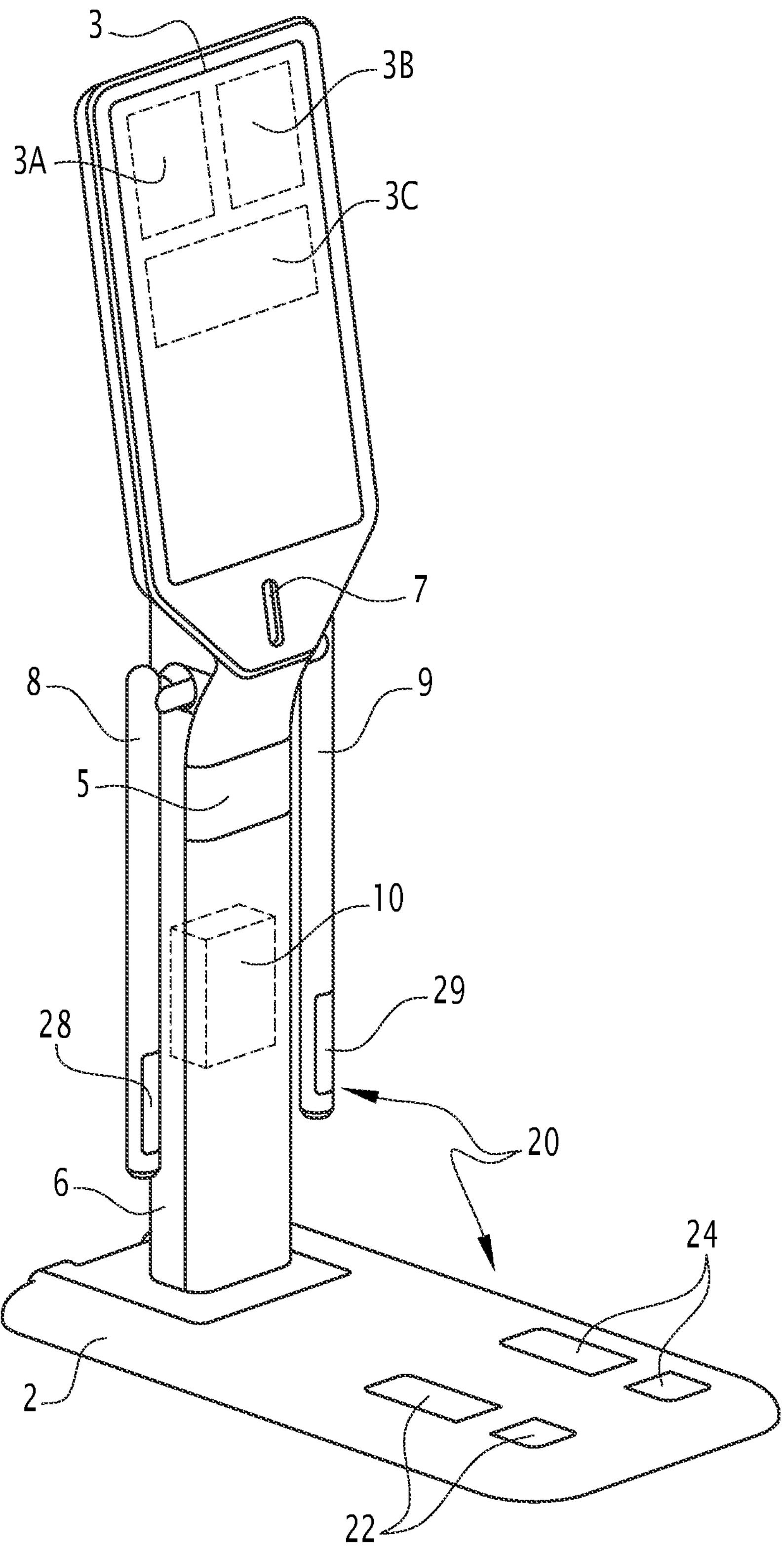
FIG. 2 is a perspective view illustrating another possible embodiment of a measurement station for assessing the functional age of a user according to the present disclosure.
Figure 3:
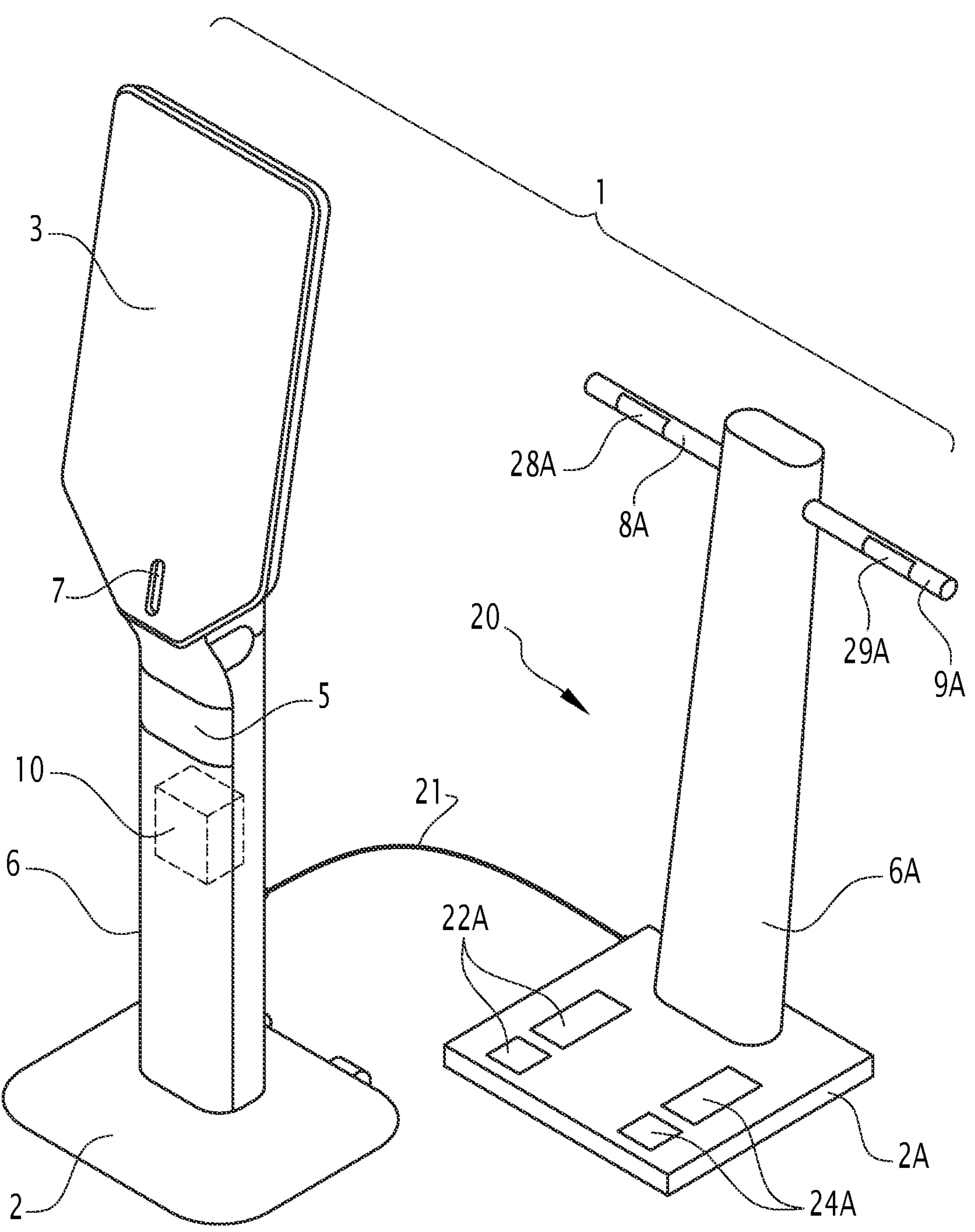
FIG. 3 is a perspective view illustrating one other possible embodiment of a measurement station for assessing the functional age of a user according to the present disclosure.

FIGS. 5 to 9 schematically illustrate some phases for testing a user performed by means of the station shown in FIG. 1 or 2 or 3.

It should be noted that in the detailed description that follows, for the purposes of clearly and concisely describing the present disclosure, the drawings may not necessarily be to scale and some characteristic features of the description may be shown in a somewhat schematic form.

Furthermore, when the term “configured”, or “adapted”, or “shaped”, or “set”, or a similar term is eventually used in the present document, in reference to any component in its entirety, or to any part of a component, or to a combination of components, it shall be understood that said term refers to and includes correspondingly the structure and/or configuration and/or shape and/or positioning.

In particular, when these terms refer to electronic hardware or software, they are to be understood as including electronic circuits or parts of electronic circuits, as well as software/firmware, such as for instance algorithms, routines and programs in general, whether they are running and/or resident in any storage medium.

Finally, in the description and in the claims that follow, the ordinal numerals first, second, et cetera, will be used purely for purposes of illustrative clarity and shall in no way be construed to be limiting for any reason whatever; in particular, the indication for example of a “second value . . . ”, or “second test”, “second device”, does not necessarily imply the presence or the stringent need for a further “first or third value”, or a “first or third test”, or “a first or third device”, and vice versa-unless it is clearly evident that such presence is needed for the correct functioning of the described embodiments; nor the need for the order to be exactly as per the described sequence (first, second, third, etc.) with reference to the exemplary embodiments illustrated herein.

FIGS. 1, 2 and 3 are perspective views illustrating three possible embodiments of a measurement station for assessing the functional age of a user according to the present disclosure, indicated in these figures by the overall reference number 1.

The definition of the measurement station 1 herein is intended to be understood as including either an apparatus that is constructed as one single structure (see, for example, FIGS. 1 and 2) which integrates the various components/constituent parts; or an apparatus that is constructed by means of two or more separate parts/devices which are connected to each other (see, for example, FIG. 3), and in the latter case it may be considered, for example, as comprising of two or more measurement substations.

Figure 4:
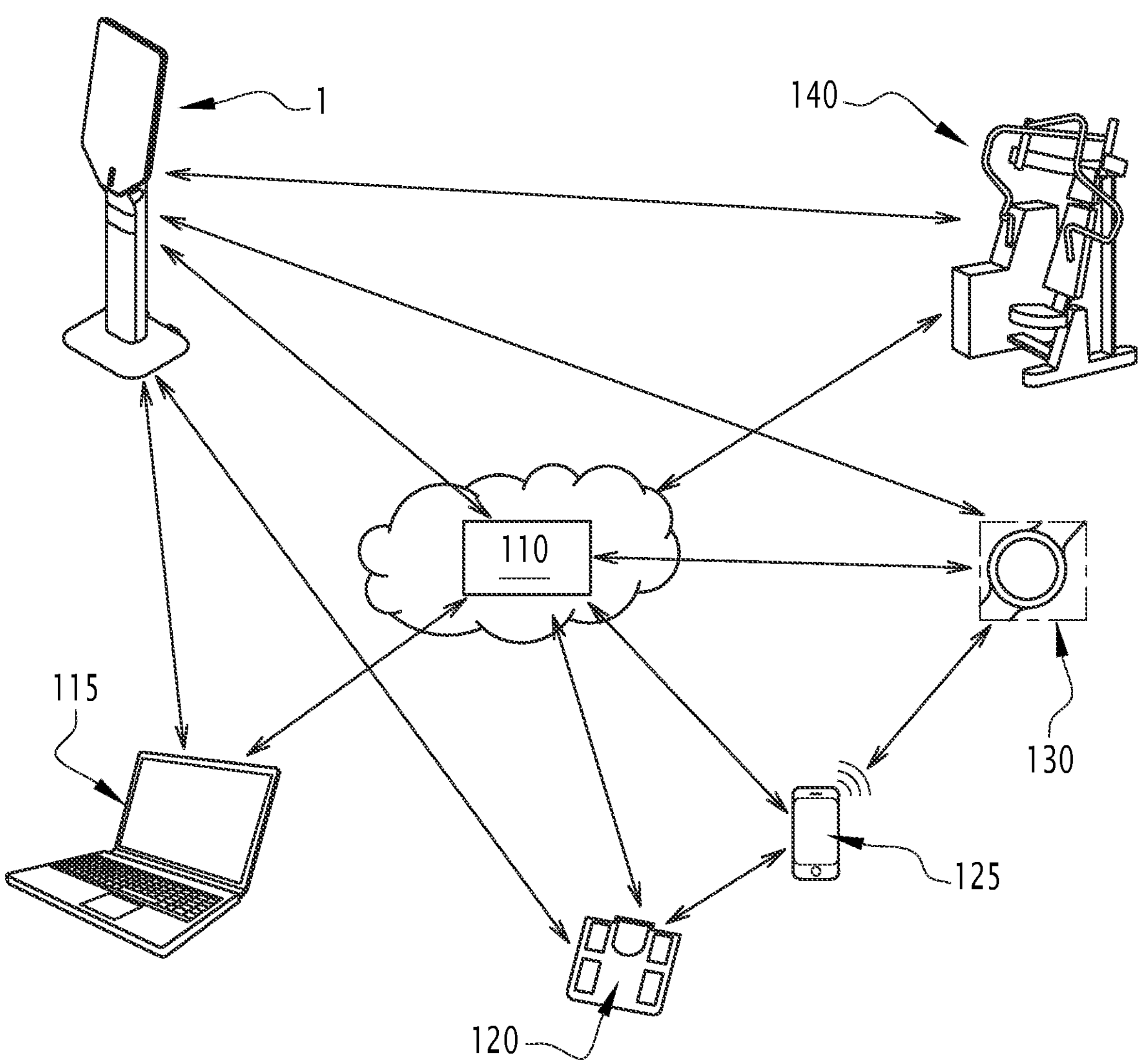
FIG. 4 is a block diagram which schematically illustrates a system for assessing the functional age of a user according to the present disclosure, which may use the measurement station shown in FIG. 1 or 2 or 3.

In particular, as it will become clear in more detail from the following description, depending on the applications, the measurement station 1 according to the disclosure may be configured as a whole so as to assess the functional age of users in a completely autonomous and self-sufficient manner, i.e. without the use/intervention of other devices not belonging to the station, it may be configured so as to assess the functional age of users also in a collaborative manner with one or more devices that are either connected to it or operatively associated with it, or else completely external, i.e. not forming part of the station, or it may also be configured as a component of a system configured as a whole so as to assess the functional age of users, an example of which is schematically illustrated in FIG. 4 and indicated therein by the global reference number 100.

Usefully, the measurement station 1 according to the disclosure includes:

at least one of a display 3 and a loudspeaker 5, preferably both;

at least one controller, represented schematically in FIGS. 1-3 by the dashed-line box 10, which is configured to present, via the display 3 and/or the loudspeaker 5, a plurality of instructions designed to guide a user in the performance of at least:

a first test designed for assessing a current level of mobility of at least one part of the body of the user;

a second test designed for assessing a current level of the balance ability of the user;

a camera 7 configured to capture and send to the controller 10 one or more images of the user when it is performing said first and second tests.

For example, in the embodiments illustrated in FIGS. 1 to 3, the measurement station 1 comprises at least one support base 2, a support 6 that rises from the support base 2 and along which the loudspeaker 5 is arranged.

The display 3 is for instance arranged at the other end of the support 6 opposite the end attached to the support base 2; for example, the camera 7 is arranged at the base of the display 3.

The camera 7 may for example be a 2D digital camera, a 3D digital camera, an RGB camera, an RGB-D camera, a video camera, a depth video camera, a TOF (Time-Of-Flight) camera, a webcam, a thermal imaging camera, etc.

Conveniently, the controller 10 is further configured so as to perform at least one of the following steps or functions:

(a): calculate a first functional age value based on the one or more images captured while the user is performing the first test, a second functional age value based on the one or more images captured while the user is performing the second test, and subsequently thereafter calculate an overall functional age value of the user at least based on the said first and second functional age values; or send the said first and second calculated functional age values to a remote controller, indicated in FIG. 4 by the reference number 110, that is configured to calculate an overall functional age value of the user at least based on said first and second functional age values sent;

(b): send, the one or more images or data related to the images captured by the camera 7 during the execution of the first test and the second test, to a remote controller 110 that is configured to calculate a first and a second functional age values based on the one or more images captured or said data related to the captured images during the execution of the first and second tests, respectively, and an overall functional age value of the user at least based on the said first and second calculated functional age values.

The controller 10 may be formed of or comprise an electronic control unit that includes, for example a processor; one or more software modules or algorithms that, when executed by the processor, will enable the various functionalities envisaged for the controller 10 to be performed, one or more communication modules for transceiving of data with the external environment, for example with the remote controller 110, and with other devices, such as, for example, the devices illustrated in FIG. 4.

The controller 10 may also comprise, for example, at least one or more local data storage units.

As for the remote controller 110 it may comprise or be formed of, for example, one or more servers either based on so-called cloud computing or operating in such a modality.

For example, initially, a user who wishes to be tested may interact with or connect directly to the station 1, or to the remote controller 110 that is operationally connected to the station 1, and possibly access this/her own data if these already exist, e.g. by means of his/her smartphone that reads a QR code on the display 3, or by simply entering their own identification data, e.g. username and password.

The data of the user may also be downloaded, for example from a PC/tablet/mobile phone, or entered manually by the user itself or by a trainer.

The user's data, relating for example to its personal profile and records concerning programs, training, state of fitness etc., may be recorded remotely, for instance in the cloud or even locally within the station 1 itself.

The display or touchscreen 3 is provided, for example, with a graphical interface that presents the user with one or more windows 3A, 3B, 3C, for guidance in performing one or more tests of interest.

Figure 5:
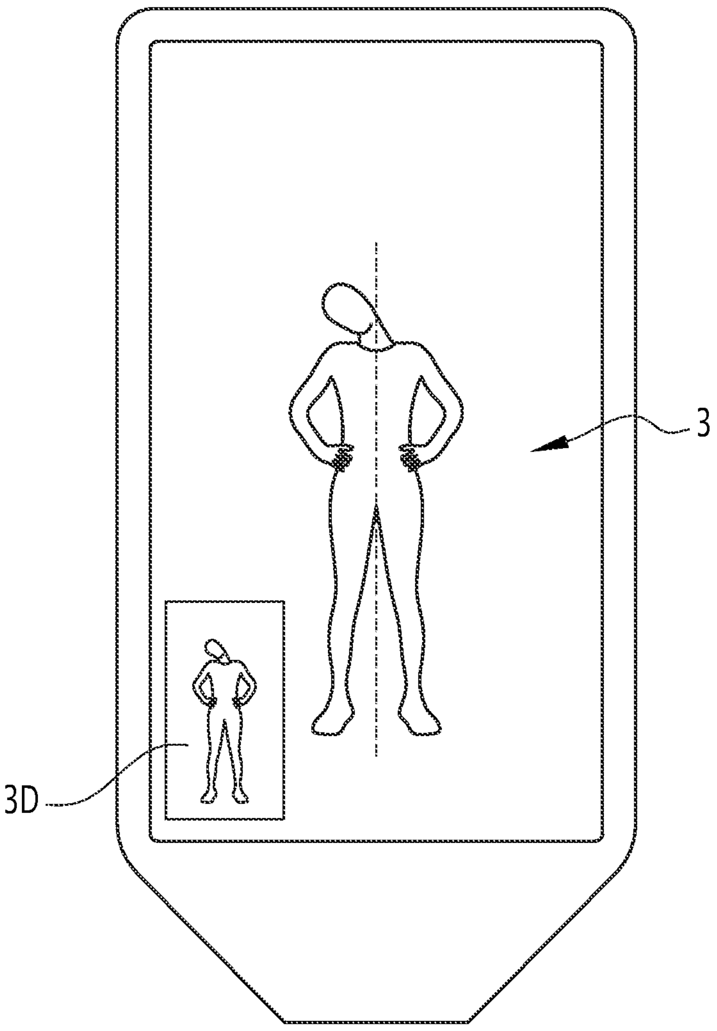
Figure 6:
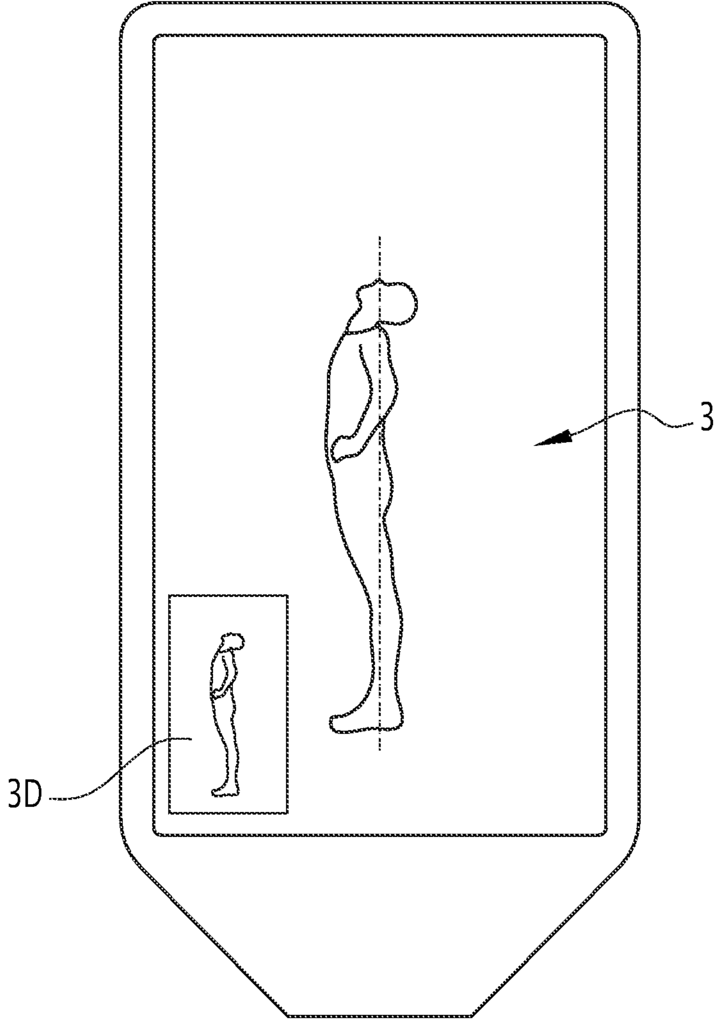
Figure 7:
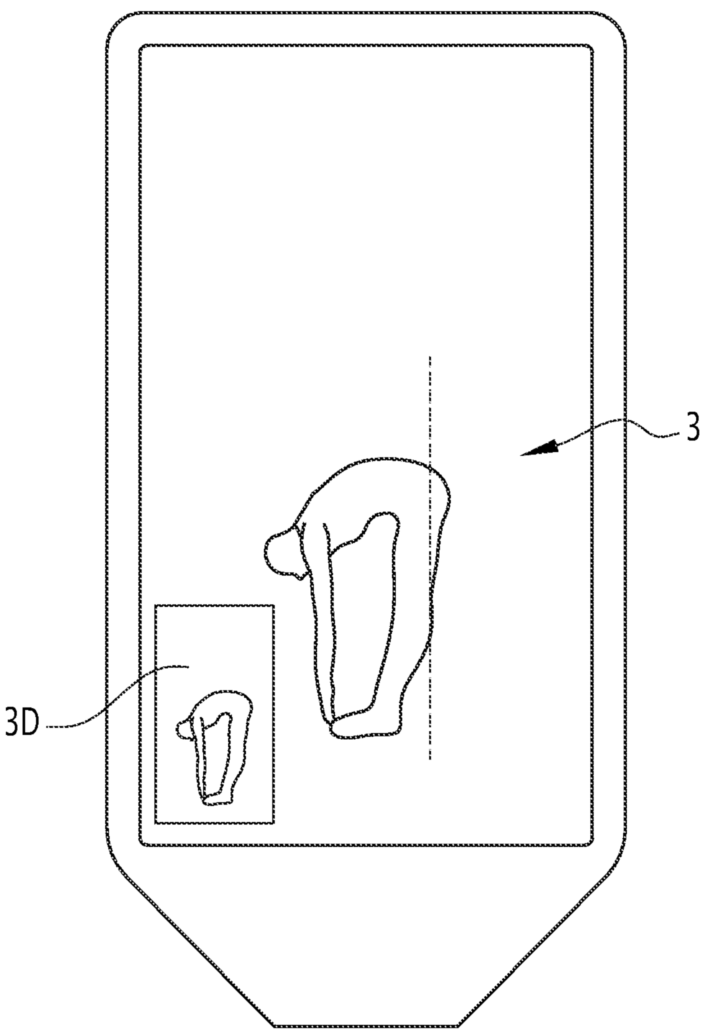
Figure 8:
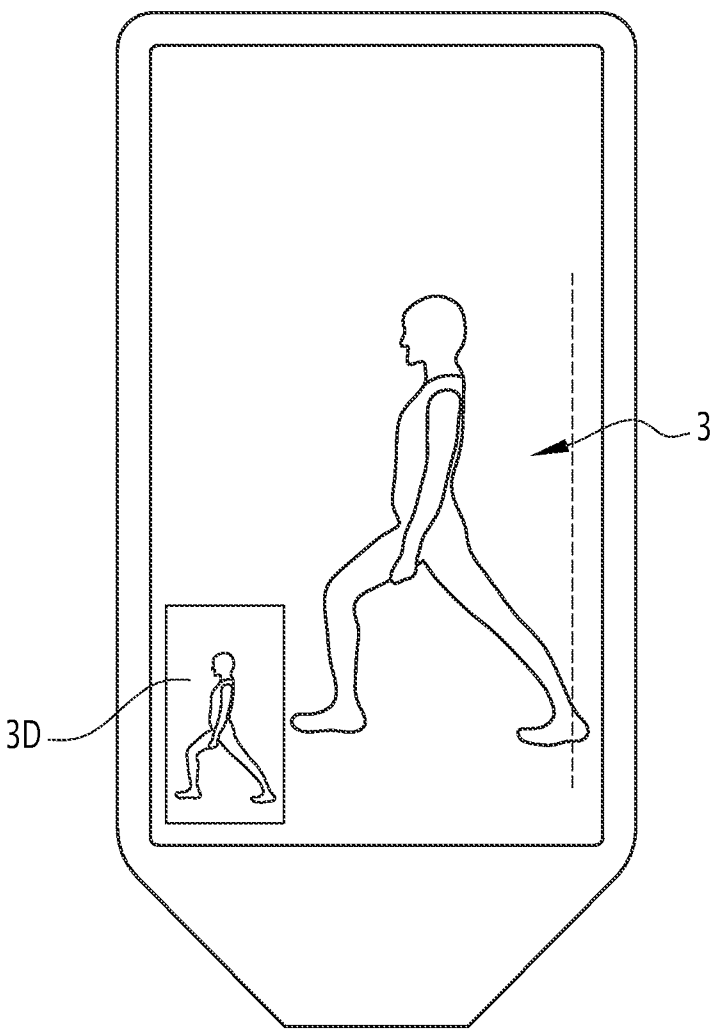

For example, when a user selects the window 3A relating to the performing of a first test designed for assessing a current level of mobility or flexibility of at least one part of the body of the user itself, the controller 10 outputs a series of instructions for performing certain movements, e.g. flexing the head to the right (and/or to the left), as illustrated in FIG. 5, extending the neck as far backwards as possible (FIG. 6), bending forward in a downward direction and maintaining the position (FIG. 7), performing a lunge with one leg forward (FIG. 8).

During the execution of the instructions received, the camera 7 captures one or more corresponding images which are sent to the controller 10 of the station 1 and/or to the remote controller 110.

For example, in one possible embodiment, the controller 10, through the use of an image/movement analysis module or algorithm, analyses the one or more images captured, proceeding thereby, for example, to calculate the angles of inclination of the parts of the body affected by the exercise and achieved by the user who is undergoing the test.

These data obtained during the test are compared by the controller 10 with the pre-recorded data, for example relating to scientific investigations/studies carried out previously, finally culminating in the computing of a first value of the functional age of the user on the basis of the results of the mobility test performed.

Similarly, the user may select the window 3B pertaining to the performing of a test designed for assessing a current level of the balance ability of the user.

Figure 9:
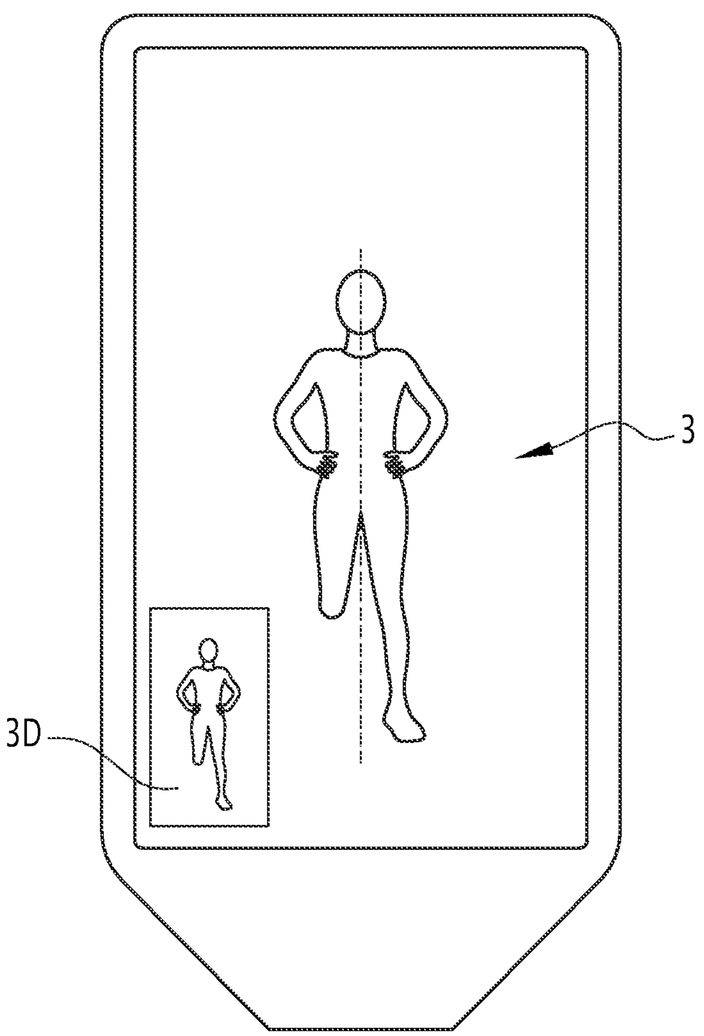

In this case, the controller 10 outputs, for example, a series of instructions for performing certain movements, e.g. lifting one foot off the ground (e.g. first the left and then the right foot) bending it towards the rear part of the thigh and maintaining the position for as long as possible or in any case for a given interval of time, as for example illustrated in FIG. 9.

Also in this case, in one possible embodiment, the controller 10, through the use of an image/movement analysis module or algorithm, which may be the same as the one used in the test of mobility or a different module, analyses the one or more images captured, thereby proceeding, for example, to calculate the length of time the user undergoing the test has maintained the required position.

In addition or alternatively, other parameters, such as the swaying of the trunk, or of the pelvis and/or legs, are recorded during a predetermined time interval, and the current level of the balance ability of the user is determined on the basis of these parameters.

The data obtained during the test are compared by the controller 10 with corresponding pre-recorded data, for example relating to scientific investigations/studies carried out previously, finally culminating in the computing of a second value of the functional age of the user on the basis of the results of the balance test performed.

During the execution of the first and second tests, the instructions output on the display 3 may be accompanied by the projection on a 3D window of the display 3 itself, of a reference image, as illustrated in FIGS. 5 to 9, and/or the instructions may be output orally through the loudspeaker 5.

In one possible embodiment of the station 1 according to the disclosure, the controller 10 is further configured to:

present, via the display 3 and/or the loudspeaker 5, a plurality of instructions designed to guide a user in performing at least a third test designed for assessing a level of cognitive ability of the user;

calculate a third functional age value based on the third test performed, and subsequently thereafter calculate an overall functional age value of the user at least based on said first, second and third functional age values; or send the third calculated functional age value to a remote controller 110, configured to calculate an overall functional age value of the user at least based on the said first, second and third functional age values sent; or alternatively, send data indicative of the third test performed or being performed by the user, to the remote controller 110 that is configured to calculate a third functional age value based on the indicative data received and an overall functional age value of the user based on said third functional age value.

For example, in accordance with this possible embodiment, when a user selects the window 3C related to the execution of a third test designed for assessing the current level of cognitive ability of a user, the controller 10 outputs a series of instructions for performing, for example, one or more sub-tests/exercises that are known per se and for this reason not described therein in detail, for example for assessing, following a sensory stimulus (e.g. visual), the current capacity for speed/accuracy of an expected response, and/or various types of memory, and/or concentration/attention ability, etc.

In this case, the display 3 serves as a direct interface for the user who can execute directly on it the exercises and/or instructions that are output.

The results of the cognitive test, expressed for instance in terms of a score, also in this case are compared by the controller 10 (and/or by the controller 110) with pre-recorded data, for example related to scientific investigations/studies carried out previously, finally culminating in the computing of a third value of the functional age of the user on the basis of the results of the of the one or more test(s) of cognitive ability performed.

In one possible embodiment, the measurement station 1 according to the disclosure further comprises a device, for example an impedance meter type device, as indicated in FIGS. 2 and 3 by the reference number 20, for measuring at least a first parameter indicative of the body mass composition of the user, such as for instance muscle mass and/or lean mass.

The first parameter measured may be, for example, the muscle mass and/or the lean mass.

In this case, the controller 10 is conveniently configured to:

- calculate a fourth functional age value based on the first measured parameter, and thereafter calculate an overall functional age value of the user also based on said fourth functional age value; or send the fourth calculated functional age value to the remote controller 110 that is configured to calculate an overall functional age value of the user also based on said fourth functional age value; and/or
- send said first measured parameter to the remote controller 110 that is configured to calculate a fourth functional age value based on said first measured parameter, and an overall functional age value of the user also based on said fourth functional age value.

The value or values of the first parameter measured in the cognitive test, expressed for example in terms of a score, also in this case are compared by the controller 10 (and/or by the remote controller 110) with pre-recorded data, for example related to scientific investigations/studies carried out previously, finally culminating in the computing of the fourth functional age value of the user on the basis of this comparison.

In particular, in one possible embodiment, as illustrated for example in FIG. 2, the measurement station 1 comprises a first arm 8 and a second arm 9 which extend from opposite sides to each other in relation to the support 6, and the device 20 is structurally integrated into the body of the station 1.

The device 20 comprises at least one pair of electrodes 22, 24 arranged on the support base 2, upon which the user stands during the measurement of the first parameter, and a first electrode 28 and a second electrode 29 which are arranged along said first arm 8 and second arm 9, respectively, and are designed to be gripped by the user in order to perform the measurement of the first parameter.

In the embodiment illustrated in FIG. 3, the measurement station 1 is in practice formed by at least two sub-units that are connected to each other and comprises a main body that substantially corresponds to the embodiment shown in FIG. 1, and the device 20 is formed by a second body that is operatively connected to the main body of the station 1, for example wired by means of one or more cables 21.

In this case, the device 20 comprises:

- an additional support base 2A;
- an additional support 6A which rises from the additional support base 2A;
- a third arm 8A and a fourth arm 9A which extend from opposite sides to each other in relation to the additional support 6A;
- at least one pair of electrodes 22A, 24A which are arranged on the additional support base 2A, and upon which the user stands during the measurement of the first parameter; and
- a third electrode 28A and a fourth electrode 29A which are arranged along the third arm 8A and the fourth arm 9A, respectively, and are designed to be gripped by the user while performing the measurement of the first parameter.

In the various embodiments illustrated in FIGS. 1 to 3, the station 1 may also comprise one or more load cells, for example integrated into the base, that are suitable for measuring the weight of a user; this data may be used by the controller 10 or the remote controller 110 in order to calculate the various functional ages or the overall functional age.

Alternatively, the measurement station 1, and in particular the controller 10 thereof is configured to:

- receive as input at least a first parameter that is measured by a device external to the station 1, and is indicative of the body mass composition of the user;
- calculate a fourth functional age value of the user based on said at least one first parameter received; and thereafter
- calculate an overall functional age value of the user also based on said fourth functional age value; or send said fourth calculated functional age value to the remote controller 110 that is configured to calculate an overall functional age value of the user also based on said fourth functional age value.

The external device, indicated schematically in FIG. 4 by the reference number 120, may be any instrument that is suitable for measuring the body mass composition of a user, for example an impedance scale.

In this case, the station 1 and/or the remote controller 110 can receive the first measured parameter, either directly from the device 120, provided that this device is equipped with communication/connection capabilities, or from a device through which the user may enter and send the measured value, for example a mobile phone as indicated in FIG. 4 by the reference number 125.

In one possible embodiment of the measurement station 1 according to the disclosure, the controller 10 is configured to:

- receive as input at least a second parameter that is measured by a device external to the station 1, and is indicative of the cardiovascular status of the user;
- calculate a fifth functional age value of the user based on said at least one second parameter received; and thereafter
- calculate an overall functional age value of the user also based on said fifth functional age value; or send the fifth calculated functional age value to the remote controller 110 that is configured to calculate an overall functional age value of the user also based on said fifth functional age value.

For example, the second parameter comprises or consists of a parameter indicative of the aerobic capacity of the user undergoing testing, e.g. his/her $VO_2$max, and may be measured by cardio exercise machines by carrying out a dedicated test, or by wearable devices, such as for instance smartwatches, an example of which is schematically illustrated in FIG. 4 with the reference number 130.

The external device 130 however may be any instrument that is suitable for measuring a parameter relating to the cardiovascular status of the user, and may be operatively connected to the station 1 and/or to the remote controller 110 of the system 1 in order to communicate this second parameter.

Also in this case, if the device 130 does not have communication or connection capabilities, this parameter may be sent from a device by means of which the user may enter and send the measured value, for example a mobile phone 125.

The value of the second measured parameter is also in this case compared by the controller 10 (and/or by the remote controller 110) with the pre-recorded data, for example relating to scientific investigations/studies carried out previously, finally culminating in the computing of the fifth functional age value of the user on the basis of this comparison.

In another possible embodiment of the measurement station 1 according to the disclosure, the controller 10 is configured to:

- receive as input at least a third parameter that is measured by a device external to the station 1, and is indicative of the muscle strength of the user;
- calculate a sixth functional age value of the user based on said at least a third parameter received; and thereafter
- calculate an overall functional age value of the user also based on said sixth functional age value; or send said sixth functional age value calculated to the remote controller 110 that is configured to calculate an overall functional age value of the user also based on the sixth functional age value.

For example, this third parameter may comprise or consist of the one-repetition maximum (commonly abbreviated to 1-RM, as per the accepted terminology), that is to say, the maximum amount of weight that can be lifted by a user for one single repetition of a given exercise, and is indicative of his/her dynamic maximal strength.

The value of the third parameter measured is also in this case compared by the controller 10 (and/or by the remote controller 110) with pre-recorded data (or dataset), for example related to scientific investigations/studies carried out previously, and/or from tests/training activities previously performed by the same user, finally culminating in the computing of the sixth functional age value of the user on the basis of this comparison.

By way of example, the construction of the dataset may be done in the manner described below.

Each time the user performs a new strength training session on gymnastic machines that have the capability of automatically monitoring the results of the training session or saving and storing the results of the training session performed (for example, manually by the user in accordance with the prescribed instructions provided to the user), the 1RM value is estimated for each set performed by means of the known formula disclosed in the literature:

$$1RM(\text{kg}) = isoWeight(\text{kg}) \cdot \begin{cases} \dfrac{36}{37 - isoRep} & \forall\ isoRep < 9 \\ \dfrac{1}{0.522 + 0.419e^{0.055\, isoRep}} & \forall\ isoRep \geq 9 \end{cases}$$

These gym machines may include, for example, a pectoral press or 'chest press', a 'leg press', and a 'vertical traction machine'.

Once the 1RM value has been calculated and saved (last saved value), the controller 10 of the station 1 and/or the controller 110 of the system 1 checks to determine whether the last saved value is an improvement over the most recently recorded value, within a predefined time window.

Following this verification, the highest value is selected as the 'valid' value.

Each time that the 1RM value is updated, it is then converted via experimental coefficients into the equivalent 1RM value for a reference exercise and/or reference equipment.

For example, the user performs a series of exercises on a flat bench and records to the cloud (i.e. within the remote controller 110 or in a data storage unit associated with the latter) or directly within the station 1, the series as "performed" with the assigned weight load.

The remote controller 110 and/or the controller 10 calculates the 1RM value for the exercise performed on the flat bench with the formula indicated above and converts this 1RM value on the flat bench press into an equivalent value of 1RM on a reference chest press, making use of a conversion coefficient. The conversion coefficients may be obtained by means of "Big Data" analysis and each coefficient is specific to the user sex/age cluster.

The same operations may be carried out for the exercises performed with the other equipment/machines used, thus obtaining a plurality of 1RM values, for example three, one for each of the three different types of equipment/machines used as indicated above.

Each of these three reference 1RM values is normalized for instance as a function of the BMI of the user, with it being possible to define a polynomial function of varying degree for each 1RM-user-gender value combination.

In this way, it is possible to construct a reference dataset (for example, static with periodic updating) in a manner such that for each normalized reference 1RM, the expected value as a function of gender and age can be obtained.

In the test phase, in the event that the specific user does not have any 1RM value already pre-recorded, it is sufficient for them to perform an exercise in order to calculate the 1RM as indicated here above. In all other cases, each time the user performs an exercise and this results in the 1RM value being higher than the value saved, this expected value is then subject to a comparison based on gender and the corresponding reference exercise.

The functional age that is closest to the calculated 1RM value is then assigned and in the event that there happen to be two possible values, the one closest to the actual chronological age is assigned.

The functional age value is assigned in this manner for each of the calculated 1RM values (three in the example above), and the overall functional age relative to muscle strength is derived by taking the average of these functional ages, e.g. among the three assigned functional ages.

In a fashion similar to that described for strength, depending on the specific applications, the controller 10 of the station 1 and/or the remote controller 110 of the system 1 are able to calculate the functional age for each of the domains or aspects being tested, such as those described here above, that is to say, balance ability, body mobility, cognitive ability, cardiovascular status, body mass composition (muscle mass and/or lean mass), and muscle strength, as an average of several values relating to the same given domain.

For example, if multiple subtests are performed in the test relating to the assessment of cognitive abilities, the controller 10 and/or the controller 110 can calculate a functional age value for each subtest performed and then calculate the third functional age value as an average computed across the values calculated for the various subtests.

Similarly, the overall functional age value may be calculated as an average across the various functional age values for each of the domains or aspects tested and taken into consideration.

Depending on the applications and the specific needs, the controller 10 is able to calculate the overall value of the functional age, solely on the basis of the first and second calculated functional age values, or is able to calculate it taking into account, in any possible combination, one or more of the other functional age values considered and described above, that is to say, the third value, the fourth value, the fifth value, and the sixth value.

In one possible embodiment of the measurement station 1 according to the disclosure, the controller 10 is conveniently configured to define, at least partially, and/or to present to a user, one or more training programs based on at least one of: said overall functional age value, and/or the first, and/or second, and/or third, and/or fourth, and/or fifth, and/or sixth functional age values calculated for the user.

These programs may be defined in an autonomous manner by the controller 10 or by the remote controller 110, and/or by means of a trainer's contribution.

In practice, the controller 10 (or the controller 110) can define, at least partially, and/or present to the user via a window on the display 3, one or more training sessions/exercises to be performed, based on the overall functional age value calculated, or one or more training sessions/exercises specifically aimed at improving separately one or more of the functional age values calculated for each domain or aspect being tested, including exercises/training of a physical nature aimed at improving the cognitive ability tested.

In particular, in one possible embodiment, as an alternative to or in combination with all of the indications provided above, a training program may also be defined on the basis of the results of a single test and/or subtest. For example, in the event that a neck mobility test is performed, if the measured angle is below an 'ideal' threshold value, the suggested training program would include exercises to enhance neck mobility. In the same way, if in the balance test the measured sway of the trunk or other body part is high, the suggested training program would include exercises to augment the balance ability. Thus, if the tests/subtests for the various domains reveal evidence of 'weaknesses' in comparison to 'ideal' values, the suggested training program would then conveniently include exercises that could potentially improve upon and compensate for these specific weaknesses.

As previously indicated, the measurement station 1 can be configured and used as a component of the system 100 illustrated in FIG. 4.

In particular, in one possible embodiment the system 100 comprises:

- a measurement station 1 configured, as previously described, to at least carry out a first test designed for assessing a current level of mobility of at least one part of the body of the user, and a second test designed for assessing a current level of the balance ability of the user;
- a remote controller 110 capable of being placed in communication with the measurement station 1 and configured at least to:
- receive in input from the measurement station 1 data related to one or more images captured while the user is performing a first test designed for assessing a current level of mobility of at least one part of the body of the user; and a second test designed for assessing a current level of the balance ability of the user;
- calculate a first and a second functional age values based on the one or more images captured while the user is performing the first and second tests, respectively, and an overall functional age value of the user at least based on said first and second calculated functional age values.

For example, in one possible embodiment, the images captured by the camera 7 are processed at least partially within the station 1, and in particular by the controller 10.

In practice, several frames per second are captured and for each frame the points of interest, the so-called nodes or 'key points', are extracted, e.g. the body of the user is schematized with a structure consisting of segments that are connected to each other by nodes at joints or other important points. The structure may have a greater or lesser density of nodes. The extracted key points are compared with 'ideal' reference key points, and the collected data relating to the key points and to the respective assessments, for all frames, are then sent to the remote controller 110.

In the remote controller 110, the collected data received are compared with the corresponding most recently saved data for the specific user in order to verify whether it is necessary to recalculate the functional age, which is to be carried out in the event that at least one item from the current data is different from the most recently saved data.

The results of the tests/subtests, for instance the values of the angles of neck inclination for mobility etc., with the associated functional age are then sent from the remote controller 110 to the 1 station in order to be displayed.

In one possible embodiment, the system 100 comprises:

- a first device, indicated in FIG. 4 by the reference number 115, which is adapted to be placed in communication with and send to the remote controller 110 data indicative of at least a third test, performed or being performed by the user, which test is adapted so as to assess a level of cognitive ability of the user; and wherein the remote controller 110 is further configured to calculate a third functional age value on the basis of indicative data received from the first device 115, and an overall functional age value of the user also on the basis of said third functional age value.

The device 115 may be any device that is suitable for the purpose, for example a computer, a tablet, a portable PC, a smartphone, etc.

Alternatively, the station 1 may be configured to perform said third test designed for assessing a level of cognitive ability of the user as previously described.

In this case, the remote controller 110 is further configured to;

- receive in input from the station 1 data indicative of the third test performed or being performed by the user;
- calculate a third functional age value on the basis of said data indicative of the third test received and an overall functional age value of the user also on the basis of said third functional age value.

In one possible embodiment, the system 100 comprises:

a second device 120, configured to measure at least a first parameter indicative of the body mass composition of the user, and wherein the remote controller 110 is configured to:

receive as input said first parameter, directly from the second device 120, or for example from a device, such as a mobile phone 125, that is capable of communicating the first measured parameter; and calculate a fourth functional age value based on said first measured parameter, and an overall functional age value of the user also based on said fourth functional age value.

Alternatively, the measurement station 1 may be configured to comprise the device 20 that is capable of measuring said first parameter which is indicative of the body mass composition of the user.

In this case, the remote controller 110 is further configured to:

receive as input from the station 1 data indicative of the first measured parameter which is indicative of the body mass composition of said user;

calculate a fourth functional age value and an overall functional age value of the user also based on said fourth functional age value.

In one possible embodiment, the system 100 comprises:

a third device, as schematically represented in FIG. 4 by the reference number 130, which is configured to measure at least a second parameter which is indicative of the cardiovascular status of said user, and wherein the remote controller 110 is configured to:

receive as input said second parameter from the third device 130 or from a device that is capable of communicating said second measured parameter; and calculate a fifth functional age value based on said second measured parameter, and an overall functional age value of the user also based on said fifth functional age value.

In one possible embodiment, the system 100 comprises at least:

a fourth device, as indicated in FIG. 4 by the reference number 140, which is configured to allow the user to perform at least one additional test designed for measuring at least a third parameter which is indicative of the muscle strength of said user; and wherein said remote controller 110 is configured to:

receive as input from said fourth device 140 at least data indicative of the additional test performed or being performed by the user; and calculate a sixth functional age value based on the at least one additional test performed, and thereafter calculate an overall functional age value of the user also based on said sixth functional age value.

The definition of fourth device 140 is to be understood as including one or more machines/equipment that are suitable for carrying out the exercises necessary for performing the strength tests and preferably configured in a manner to be in operational communication with the remote controller 110 and the measurement station 1.

For example, the device 140 may include one or more of the aforementioned exercise machines, e.g. a chest press, a leg press, and a vertical traction machine.

Depending on the applications and the specific needs, the remote controller 110 is able to calculate the overall value of the functional age, solely on the basis of the first and second calculated functional age values, or is able to calculate it taking into account, in any possible combination, one or more of the other functional age values considered and described above, that is to say, the third value, the fourth value, the fifth value, and the sixth value.

In one possible embodiment of the system 100 according to the disclosure, the remote controller 110 is configured to set, at least partially, and/or to present to the user, one or more training programs based on at least one of: the overall functional age value, and/or said first, and/or second, and/or third, and/or fourth, and/or fifth, and/or sixth functional age values calculated for the user.

These programs may be defined in an autonomous manner by the remote controller 110, and/or by means of the contribution of a trainer.

In practice, the controller 110 is able to at least partially set or define, and/or present to the user, for example via a window on the display 3, or on a device used by the user, one or more training sessions/exercises to be performed, based on the overall functional age value calculated; or one or more training sessions/exercises specifically aimed at improving separately one or more of the functional age values calculated for each domain or aspect being tested, including exercises/training of a physical nature aimed at improving the cognitive ability being tested.

In practice, it has been found that the measurement station 1 and the system 100 for assessing the functional age of a user according to the disclosure allow achieving the intended object since they make it possible to calculate the functional age of users by taking into account a number of aspects and on the basis of a larger dataset, and thus provide a more precise and reliable value.

In addition, the station 1 and/or the system 100 are not limited to only calculating the individual functional ages and the overall functional age, but also provide users with a customized training plan aimed at augmenting both the overall functional age value and the functional age value calculated for each of the physical and mental aspects considered, including the aspects related to each of the tests/subtests performed.

Clearly, without prejudice to the principle of the disclosure, the embodiments and details of implementation may vary widely with respect to what has been described and illustrated purely by way of not limiting examples, without thereby departing from the scope of protection of the present disclosure as defined by the appended claims.

The invention claimed is:

1. A measurement station for assessing the functional age of a user, said measurement station comprising:

at least one display and/or a loudspeaker;

at least one controller configured to present, via said display and/or said loudspeaker, a plurality of instructions which guide a user to perform a method comprising:

conducting a first test adapted to assess a current level of mobility of at least one part of the body of the user;

conducting a second test designed to assess a current level of the balance ability of the user;

using a camera configured to capture and send to the controller one or more images of the user when conducting said first and second tests: wherein said at least one controller is further configured to perform a method comprising:

(a) schematizing the user's body with a structure consisting of segments that are connected to each other by reference nodes;

(b) calculating a first functional age value based on the one or more images captured by comparing nodes extracted from the one or more images captured while performing the first test with said reference nodes, and a second functional age value based on the one or more images captured while performing the second test, and thereafter calculating an overall functional age value of the user at least based on said first and second functional age values or send said first and second calculated functional age values to a remote controller configured to calculate an overall functional age value of the user at least based on said first and second functional age values sent; and (c): sending data related to said one or more images captured during the execution of the first test and the second test to a remote controller configured to calculate a first and a second functional age values based on the data related to the one or more images captured during the execution of the first and second tests, respectively, and an overall functional age value of the user at least based on said first and second calculated functional age values.

2. The measurement station according to claim 1, further comprising a device for measuring at least a first parameter indicative of the body mass composition said user, and wherein said controller is configured to:

calculate a fourth functional age value based on said first measured parameter, and thereafter calculate an overall functional age value of said user also based on said fourth functional age value or send said fourth calculated functional age value to said remote controller configured to calculate an overall functional age value of said user also based on said fourth functional age value; or alternatively, send said first measured parameter to said remote controller configured to calculate a fourth functional age value based on said first measured parameter, and an overall functional age value of the user also based on said fourth functional age value.

3. The measurement station according to claim 2, comprising a support base, a support rising from said support base and at the opposite end of which, with respect to the support base, there is disposed a display, a first arm and a second arm extending from opposite sides to each other with respect to the support, and wherein said device comprises at least one pair of electrodes arranged on said support base, and an additional first electrode and an additional second electrode which are arranged along said first arm and second arm, respectively.

4. The measurement station according to claim 2, comprising a main body having a support base, a support rising from said support base and at the opposite end of which, with respect to said support base, there is disposed a display, and a device for measuring at least a first parameter indicative of the body mass composition of said user, said device being operatively connected to said main body and comprising a further support base, an additional support rising from said additional support base, a third arm and a fourth arm extending from opposite sides to each other with respect to said additional support, at least one pair of electrodes arranged on said additional support base, and an additional third electrode and an additional fourth electrode being arranged along said third arm and fourth arm, respectively.

5. The measurement station according to claim 1, wherein said controller is further configured to:

receive as input at least a first parameter measured by an external device and indicative of the body mass composition of said user;

calculate a fourth functional age value of said user based on said at least a first parameter received; and thereafter calculate an overall functional age value of the user also based on said fourth functional age value or send said fourth calculated functional age value to said remote controller configured to calculate an overall functional age value of the user also based on said fourth functional age value.

6. The measurement station according to claim 1, wherein said controller is further configured to:

receive as input at least a second parameter measured by an external device and indicative of the cardiovascular status of said user;

calculate a fifth functional age value of the user based on said at least a second parameter received; and thereafter calculate an overall functional age value of the user also based on said fifth functional age value or send said fifth functional age value calculated to said remote controller configured to calculate an overall functional age value of the user also based on said fifth functional age value.

7. The measurement station according to claim 1, wherein said controller is further configured to:

receive as input at least a third parameter measured by an external device and indicative of the muscle strength of said user;

calculate a sixth functional age value of the user based on said at least one third parameter received; and thereafter calculate an overall functional age value of the user also based on said sixth functional age value or send said sixth functional age value calculated to said remote controller configured to calculate an overall functional age value of the user also based on said sixth functional age value.

8. The measurement station according to claim 1, wherein said controller is configured to at least partially set, and/or present to the user, one or more training programs for said user based on at least one of said overall functional age value and/or said first, and/or second, and/or third, and/or fourth and/or fifth and/or sixth functional age values calculated for said user.

9. The measurement station according to claim 1, wherein said measurement station is further configured to:

present, via said display and/or said loudspeaker, a plurality of instructions designed to guide a user in performing at least a third test designed to assess a level of cognitive ability of the user; and calculate a third functional age value based on the third executed test, and thereafter calculating an overall functional age value of the user at least based on said first, second and third functional age values, or sending said third calculated functional age value to a remote controller configured to calculate an overall functional age value of the user at least based on said first, second and third functional age values sent; or alternatively, send data indicative of the third test performed or being performed by the user to said remote controller configured to calculate a third functional age value based on the received data indicative of the third test and an overall functional age value of the user based on said first, second and third functional age values.

10. A system for assessing the functional age of a user, comprising:

a measurement station configured according to claim 1;

a remote controller suitable for being placed in communication with said measurement station;

and wherein said remote controller is configured to:

receive in input from the measurement station data related to one or more images captured while performing a first test suitable for assessing a current level of mobility of at least one part of the body of the user, and a second test suitable for assessing a current level of the balance ability of the user;

calculate a first and a second functional age values on the basis of said data related to the one or more images captured during the performance of the first and second tests, respectively, and an overall functional age value of the user at least on the basis of said calculated first and second functional age values.

11. The system according to claim 10, comprising:

a first device which is adapted to be put in communication with and send to said remote controller data indicative of at least a third test performed or being performed by the user, said third test being adapted to assess a level of cognitive ability of said user; and wherein said remote controller is further configured to calculate a third functional age value on the basis of data indicative of the third test received from the first device and an overall functional age value of the user also on the basis of said third functional age value.

12. A system for assessing the functional age of a user, comprising at least:

a measurement station configured according to claim 1;

a remote controller suitable for being placed in communication with said measurement station;

and wherein said remote controller is configured at least to:

receive in input from the measurement station data related to one or more images captured while performing a first test suitable for assessing a current level of mobility of at least one part of the body of the user, and a second test suitable for assessing a current level of the balance ability of the user;

calculate a first and a second functional age values on the basis of said data related to the one or more images captured during the performance of the first and second tests, respectively, and an overall functional age value of the user at least on the basis of said calculated first and second functional age values, and wherein said remote controller is further configured to:

receive in input from the station data indicative of the third test performed or being performed by the user, suitable for assessing a level of cognitive ability of said user;

calculate a third functional age value on the basis of said data indicative of the third test received and an overall functional age value of the user also on the basis of said third functional age value.

13. The system according to claim 10, comprising:

a second device configured to measure at least a first parameter indicative of the body mass composition of said user;

and wherein said remote controller is configured to:

receive as input said first parameter, from said second device or from a device capable of communicating said first measured parameter; and calculate a fourth value of functional age based on said first measured parameter, and an overall value of functional age of the user also based on said fourth value of functional age.

14. The system for assessing the functional age of a user, comprising:

a measurement station configured according to claim 3;

a remote controller suitable for being placed in communication with said measurement station;

and wherein said remote controller is configured at least to:

receive in input from the measurement station data related to one or more images captured while performing a first test suitable for assessing a current level of mobility of at least one part of the body of the user, and a second test suitable for assessing a current level of the balance ability of the user;

calculate a first and a second functional age values on the basis of said data related to the one or more images captured during the performance of the first and second tests, respectively, and an overall functional age value of the user at least on the basis of said calculated first and second functional age values, and wherein said remote controller is further configured to:

receive in input from station data indicative of the first measured parameter indicative of body mass composition of said user;

calculate a fourth functional age value and an overall functional age value of the user also based on said fourth functional age value.

15. The system according to claim 10, comprising:

a third device configured to measure at least a second parameter indicative of the cardiovascular status of said user;

and wherein said remote controller is configured to:

receive in input said second parameter from said third device or from a device capable of communicating said second measured parameter; and calculate a fifth functional age value based on said second measured parameter, and an overall functional age value of the user also based on said fifth functional age value.

16. The system according to claim 10, comprising:

a fourth device configured to allow the user to perform at least one additional test suitable for measuring at least a third parameter indicative of the muscle strength of said user;

and wherein said remote controller is configured to:

receive as input at least data indicative of said further test performed or being performed by said user; and calculate a sixth functional age value based on the at least one further test performed, and thereafter calculate an overall functional age value of the user also based on said sixth functional age value.

17. The system according to claim 10, wherein said remote controller is configured to set at least in part, and/or to present to the user, one or more training programs for said user based on at least one of said overall value of functional age, and/or said first, and/or second, and/or third, and/or fourth and/or fifth, and/or sixth values of functional age.

* * * * *